(12) United States Patent
Patel et al.

(10) Patent No.: US 10,544,175 B2
(45) Date of Patent: Jan. 28, 2020

(54) CRYSTALLINE FOSAPREPITANT DICYCLOHEXYLAMINE SALT AND ITS PREPARATION

(71) Applicants: Jigneshkumar Jasubhai Patel, Gujarat (IN); Raja Jeyakumar John Muthiah, Gujarat (IN)

(72) Inventors: Jigneshkumar Jasubhai Patel, Gujarat (IN); Raja Jeyakumar John Muthiah, Gujarat (IN)

(73) Assignee: Navinta, LLC, Ewing, NJ (US)

( * ) Notice: Subject to any disclaimer, the term of this patent is extended or adjusted under 35 U.S.C. 154(b) by 0 days.

(21) Appl. No.: 15/728,972

(22) Filed: Oct. 10, 2017

(65) Prior Publication Data

US 2018/0030076 A1 Feb. 1, 2018

Related U.S. Application Data

(62) Division of application No. 15/165,643, filed on May 26, 2016, now Pat. No. 9,850,267.

(60) Provisional application No. 62/170,576, filed on Jun. 3, 2015.

(51) Int. Cl.
*C07F 9/6558* (2006.01)
*A61K 31/675* (2006.01)
*C07C 211/35* (2006.01)

(52) U.S. Cl.
CPC ........ *C07F 9/65583* (2013.01); *A61K 31/675* (2013.01); *C07C 211/35* (2013.01); *C07F 9/65586* (2013.01); *C07C 2601/14* (2017.05)

(58) Field of Classification Search
None
See application file for complete search history.

(56) References Cited

U.S. PATENT DOCUMENTS

| 7,915,407 | B2 | 3/2011 | McNamara et al. |
| 8,623,844 | B2 | 1/2014 | Bhatt et al. |
| 2011/0130366 | A1 | 6/2011 | Bhatt et al. |
| 2014/0107337 | A1 | 4/2014 | Reddy et al. |

FOREIGN PATENT DOCUMENTS

WO 2010018595 A2 2/2010

*Primary Examiner* — Po-Chih Chen
(74) *Attorney, Agent, or Firm* — St. Onge Steward Johnston & Reens LLC

(57) ABSTRACT

Dicyclohexylamine salt of fosaprepitant (fosaprepitant DCHA), a process for preparing fosaprepitant DCHA, and a use of fosaprepitant DCHA in the preparation of pharmaceutically acceptable fosaprepitant dimeglumine with high purity is provided. Fosaprepitant dimeglumine is prepared by treating fosaprepitant DCHA with an acid to form fosaprepitant, followed by adding N-methyl-D-glucamine to fosaprepitant.

18 Claims, 3 Drawing Sheets

CRYSTALLINE FOSAPREPITANT DICYCLOHEXYLAMINE SALT AND ITS PREPARATION

FIELD OF THE INVENTION

The present invention relates to dicyclohexylamine salt of fosaprepitant (fosaprepitant DCHA salt) (formula II, hereinafter "II"), a process of making fosaprepitant DCHA salt (II), and a use of fosaprepitant DCHA salt (II) in the preparation of a pharmaceutically acceptable salt, fosaprepitant dimeglumine (formula Ia, hereinafter "Ia").

BACKGROUND OF THE INVENTION

Fosaprepitant dimeglumine (Ia) is an antiemetic drug for intravenous administration. It is supplied as a sterile, lyophilized powder in a sealed vial under the trade name EMEND for injection by Merck and Co., Inc. Each vial of EMEND for injection contains 245.3 mg of fosaprepitant dimeglumine equivalent to 150 mg of fosaprepitant free acid and the following inactive ingredients: edetate disodium (18.8 mg), polysorbate 80 (75 mg), lactose anhydrous (375 mg), sodium hydroxide and/or hydrochloric acid (for pH adjustment).

Fosaprepitant dimeglumine (Ia) is a white to off-white amorphous powder with a molecular weight of 1004.83. It is freely soluble in water, which makes it particularly suitable for aqueous based intravenous administration. The active ingredient, fosaprepitant, is chemically known as {3-[2(R)-[(1R)-1-[3,5-bis(trifluoromethyl)phenyl]ethoxy]-3(S)-(4-fluorophenyl)morpholin-4-yl]methyl]-5-oxo-4,5-dihydro-[1,2,4]-triazol-1-yl}phosphonic acid (Formula I, hereinafter "I"). The structures of fosaprepitant dimeglumine (Ia) and fosaprepitant free acid (I) are depicted as follows:

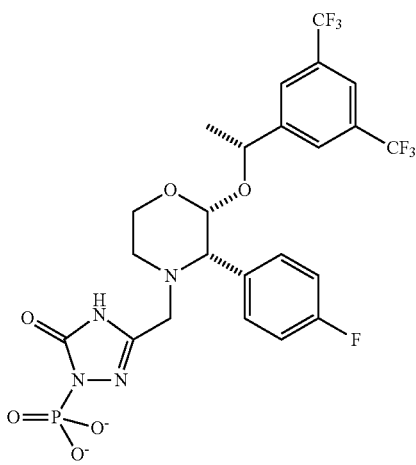

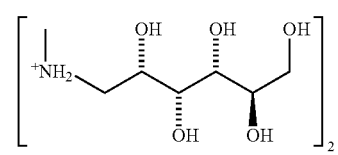

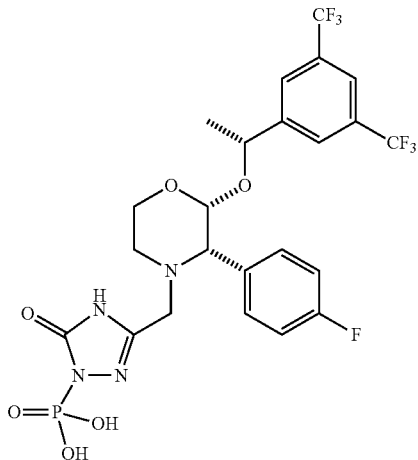

Fosaprepitant dimeglumine (Ia) and fosaprepitant free acid (I) are both a prodrug of aprepitant (formula III, hereinafter "III"), which has the following structure:

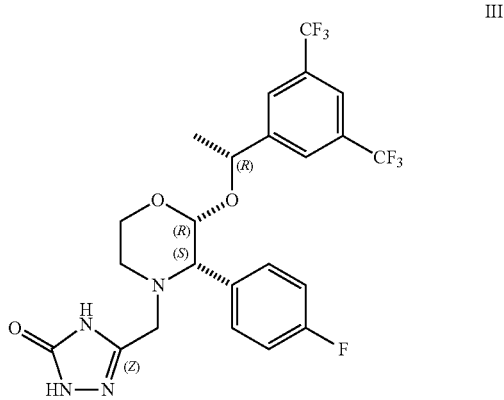

When EMEND for injection is administered via an intravenous infusion, fosaprepitant is rapidly converted in the body to aprepitant. Aprepitant is a selective high-affinity antagonist of human substance P/neurokinin-1 ($NK_1$) receptors. EMEND for injection, in combination with other antiemetic agents, is indicated in adults for the prevention of acute and delayed nausea and vomiting associated with initial and repeat courses of highly emetogenic cancer chemotherapy (HEC) including high-dose cisplatin and for the prevention of delayed nausea and vomiting associated with initial and repeat courses of moderately emetogenic cancer chemotherapy (MEC).

U.S. Pat. No. 7,915,407 discloses a process for the preparation of fosaprepitant dimeglumine. The entire content of this patent is incorporated herein by reference. The patented process comprises the steps of isolating monobenzyl{3-[2(R)-[(1R)-1-[3,5-bis(trifluoromethyl)phenyl]ethoxy]-3(S)-(4-fluorophenyl)morpholin-4-yl]methyl]-5-oxo-4,5-dihydro-[1,2,4]-triazol-1-yl}phosphonic acid (hereinafter, "monobenzyl fosaprepitant") followed by subjecting the monobenzyl fosaprepitant to hydrogenation in a cosolvent system of methanol and water in the presence of palladium on carbon and N-methyl-D-glucamine to yield fosaprepitant dimeglumine.

U.S. Pat. No. 8,623,844 discloses another process for the preparation of fosaprepitant dimeglumine, the entire content of which is incorporated herein by reference. According to the patent, fosaprepitant dimeglumine may be prepared by (1) isolation of dibenzyl{3-[2(R)-[(1R)-1-[3,5-bis(trifluoromethyl)phenyl]ethoxy]-3(S)-(4-fluorophenyl)morpholin-4-yl]methyl]-5-oxo-4,5-dihydro-[1,2,4]-triazol-1-yl}phosphonic acid (hereinafter, "dibenzyl fosaprepitant"), (2) hydrogenation of dibenzyl fosaprepitant in a solvent system of methanol and water in the presence of palladium on carbon and N-methyl-D-glucamine to yield crude fosaprepitant dimeglumine, and (3) purification of crude fosaprepitant dimeglumine.

U.S. Patent Application Publication No. 20140107337 discloses a slightly different process for preparing fosaprepitant dimeglumine from that of U.S. Pat. No. 8,623,844. The entire content of this publication is incorporated herein by reference to this application. According to the publication, fosaprepitant dimeglumine can be prepared by subjecting dibenzyl fosaprepitant to hydrogenation in a solvent system of methanol in the presence of palladium on carbon, N-methyl-D-glucamine, and a silica bond metal scavenger. It is reported that, as result of using the silica bond metal scavenger, the resulting fosaprepitant dimeglumine product has a lower content of palladium.

Since fosaprepitant dimeglumine salt is highly hygroscopic in nature, it is difficult to subject fosaprepitant dimeglumine salt to purification (e.g. crystallization) on a large scale. However, purification of the precursors of fosaprepitant dimeglumine (i.e., intermediates) produced in the prior art processes is neither ideal nor practical. For example, dibenzyl fosaprepitant is not very stable and prone to an instantaneous conversion to monobenzyl fosaprepitant. Monobenzyl fosaprepitant is more stable than dibenzyl fosaprepitant but it is difficult to remove all of synthetic impurities and unused reagents from the solid of monobenzyl fosaprepitant. Additionally, fosaprepitant is prepared by catalytic hydrogenation of dibenzyl fosaprepitant or monobenzyl fosaprepitant using palladium (Pd) on carbon as a catalyst, as disclosed in the prior art. The Pd catalyst needs to be removed from fosaprepitant after the hydrogenation in order to obtain a product suitable for pharmaceutical use. But the poor stability of fosaprepitant makes the removal of the Pd catalyst very challenging.

Thus, there remains a need in the industry to provide an improved process for the preparation of fosaprepitant dimeglumine with high purity that is amenable for a commercial scale synthesis.

SUMMARY OF THE INVENTION

One object of the present invention is to provide a novel, industrial scale process using a novel intermediate or precursor for the preparation of pharmaceutically acceptable fosaprepitant dimeglumine.

Another object of the present invention is to provide a precursor of fosaprepitant dimeglumine which is stable and can be easily purified to remove excess reagents, impurities, and by-products to allow for the subsequent preparation of pure fosaprepitant dimeglumine.

A further object of the present invention is to provide an economical, efficient, and viable process for the preparation of the precursor.

The above objects have been realized by the invention and use of dicyclohexylamine salt of fosaprepitant (fosaprepitant DCHA, formula II), a crystalline, high melting point, stable solid, which can be easily isolated by routine purification techniques. Dicyclohexylamine salt of fosaprepitant contains two molecules of dicyclohexylamine for each molecule of fosaprepitant. It is therefore also referred as fosaprepitant di(dicyclohexylamine). The present application uses the terms, dicyclohexylamine salt of fosaprepitant, fosaprepitant DCHA, fosaprepitant DCHA salt, fosaprepitant di(dicyclohexylamine), fosaprepitant di(dicyclohexylamine) salt, fosaprepitant dicyclohexylamine, and fosaprepitant dicyclohexylamine salt, interchangeably. The structure of formula II is depicted as follows:

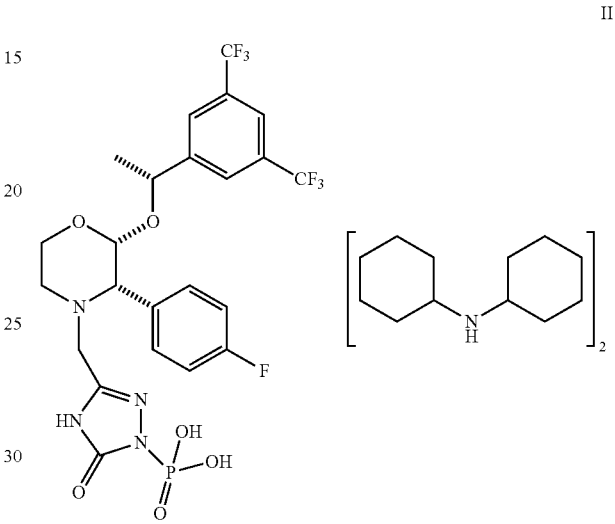

II

Different from the prior art process, the production and purification of fosaprepitant DCHA (II) occur at a later stage, after the catalytic hydrogenation step, in the manufacturing process of fosaprepitant dimeglumine, which allows for the preparation of fosaprepitant dimeglumine with high purity and yield.

In one aspect, the present invention provides a process for the preparation of fosaprepitant DCHA salt (II). The process comprises the steps of reacting aprepitant (III) with tetrabenzyl pyrophosphate in the presence of a base and a solvent to obtain dibenzyl fosaprepitant; hydrogenating the dibenzyl fosaprepitant in the presence of 10% Pd/C, dicyclohexylamine, and a solvent system to form fosaprepitant DCHA salt (II), followed by isolating fosaprepitant DCHA salt (II). In some embodiments, basic alumina is added in the hydrogenation reaction mixture.

Fosaprepitant DCHA salt (II) prepared by the process of the present invention has an HPLC purity of greater than or equal to 99.0%, preferably, greater than 99.5%; more preferably, greater than 99.85%; and even more preferably, greater than 99.9%.

In another aspect, the present invention provides a crystalline form of fosaprepitant DCHA salt (II) having an X-ray powder diffraction pattern with peaks at about 4.52, 8.29, 13.17, 17.23, 18.31, and 22.51±0.2° 2θ.

In another aspect, the present invention provides a crystalline form of fosaprepitant DCHA salt (II) having Fourier transform IR spectra with absorptions at about 1061, 1133, 1170, 1281, 1450, 1509, 1678, 2525, 2858, 2937, and 3395 cm$^{-1}$.

In a further aspect, the present invention provides an improved process for the preparation of fosaprepitant dimeglumine (Ia) that is free or substantially free of organic and inorganic impurities, in particularly, free of heavy metal such as palladium, by using fosaprepitant DCHA salt (II) as an intermediate. The process comprises the steps of: preparing fosaprepitant DCHA salt (II) as described earlier; treating a solution of fosaprepitant DCHA salt (II) with an acid to obtain fosaprepitant (I); dissolving fosaprepitant (I) and N-methyl-D-glucamine in a solvent to obtain fosaprepitant di(N-methyl-D-glucamine) salt (Ia); and isolating fosaprepitant di(N-methyl-D-glucamine) salt (Ia).

Fosaprepitant di(N-methyl-D-glucamine) salt (Ia) prepared by the process of the present invention has an HPLC purity of greater than or equal to 99.0%, preferably, greater than 99.5%; more preferably, greater than 99.85%; and even more preferably, greater than 99.9%.

DETAILED DESCRIPTION OF THE INVENTION

Figure 1:
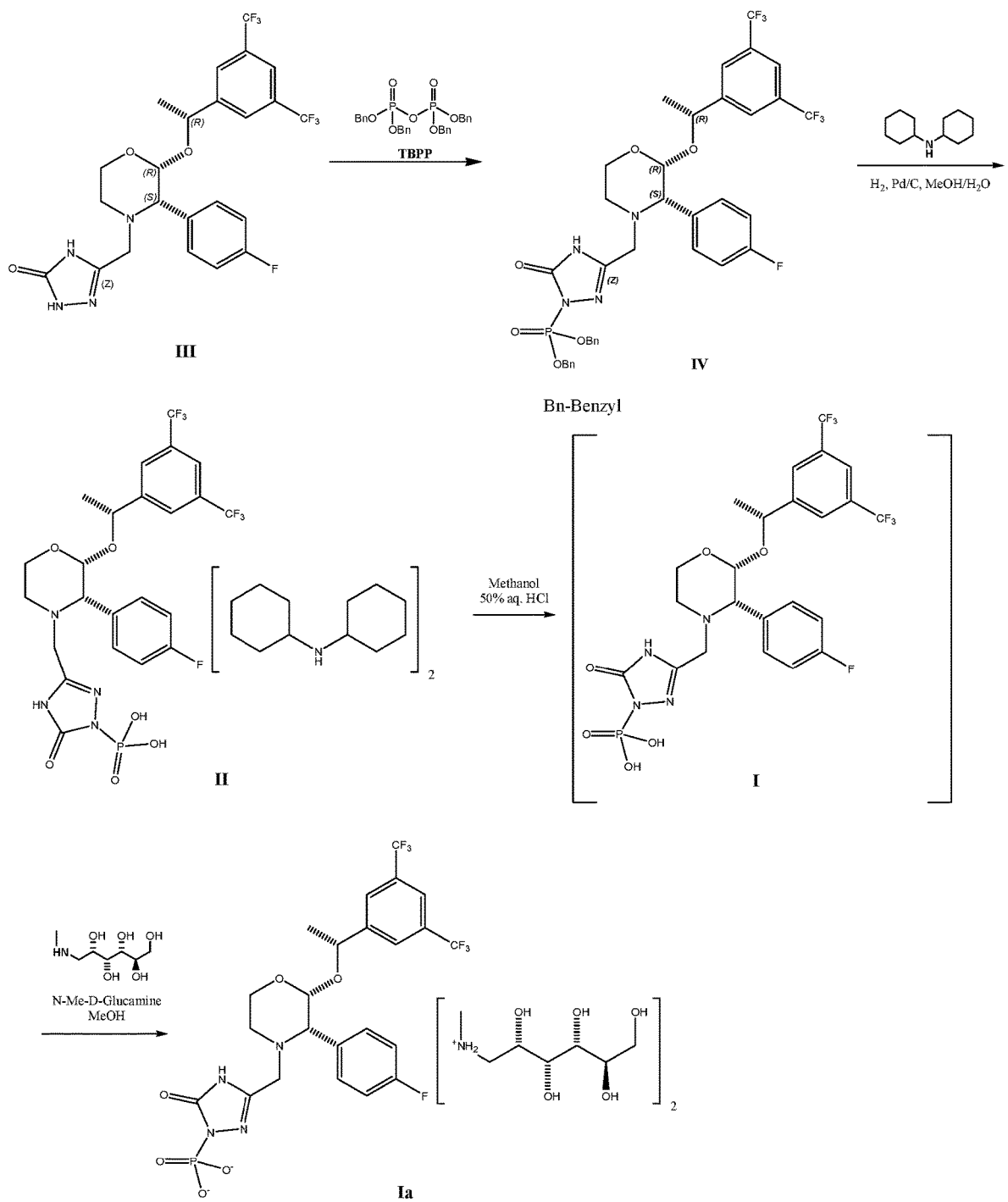
FIG. 1 shows a synthetic scheme for the preparation of fosaprepitant dimeglumine (Ia) by using fosaprepitant DCHA salt (II) as an intermediate according to one embodiment of the invention.

FIG. 1 shows a synthetic scheme for the preparation of fosaprepitant DCHA salt (II) and the preparation of fosaprepitant dimeglumine (Ia) by using fosaprepitant DCHA salt (II) as a precursor.

According to FIG. 1, the process for preparing fosaprepitant dimeglumine (Ia) starts with aprepitant (III). A reaction of aprepitant (III) with tetrabenzyl pyrophosphate (TBPP) in the presence of a base and a suitable solvent gives dibenzyl fosaprepitant (formula IV, hereinafter "IV"). Dibenzyl fosaprepitant (IV) is subjected to debenzylation with 10% Pd/C in the presence of dicyclohexyl amine, a solvent system, under a hydrogen pressure, to give dicyclohexylamine salt of fosaprepitant (II), a high melting solid. In some embodiments, basic alumina is added in the hydrogenation reaction mixture to moderate the activity of the catalyst.

As known by a person of ordinary skill in the art, the debenzylation reaction may also be called hydrogenation reaction. Any known solvent system suitable for hydrogenation reaction may be used to in the reaction which converts dibenzyl fosaprepitant (IV) to fosaprepitant DCHA (II). Preferably, the solvent system for the hydrogenation or debenzylation reaction is a mixture of an organic solvent and water; more preferably, the solvent system is a mixture of methanol and water. In addition to 10% Pd/C, any catalyst that is suitable for debenzylation can be used in the reaction.

In accordance with some embodiments, the debenzylation reaction comprises the steps of:

1. catalytic reduction of dibenzyl fosaprepitant (IV) in an aprotic or protic solvent, such as ethyl acetate, methyl-tert-butyl ether, methanol, isopropanol, or a similar solvent or a mixture of the solvents, with 10% Pd/C (50% wet) in presence of basic alumina, dicyclohexylamine, and water under a hydrogen pressure;

2. maintaining the reaction mass of step 1 under a hydrogen pressure at a temperature in the range from about 15° C. to about 50° C., preferably from about 25° C. to about 35° C., for about 1 to about 12 hours, preferably about 2 to about 3 hours; followed by filtration to remove the catalyst and alumina, which produces fosaprepitant dicyclohexylamine salt (II) in a filtrate solution;

3. concentrating (such as by evaporating or other known methods) the filtration solution of step 2 at a temperature in the range from about 25° C. to about 35° C., followed by addition of another suitable solvent system, preferably acetone, methyl ethyl ketone, acetonitrile, ethyl acetate, or mixture of two or more of the solvents, and filtering to isolate the fosaprepitant dicyclohexylamine salt (II); and 4. optionally, recrystallization of the compound, fosaprepitant dicyclohexylamine salt (II), obtained in step 3.

Fosaprepitant dicyclohexylamine (II) may be recrystallized by dissolving it in a suitable solvent, such as methanol, ethanol, isopropyl alcohol, n-butanol, and the like, or a mixture of the solvents, at a temperature of about 25° C. to about 60° C., and then crystallizing and isolating the solid by using the convenient techniques, such as cooling, partial or complete removal of solvent from the solution, adding anti-solvent, seeding, or combination thereof. A second or third recrystallization of fosaprepitant dicyclohexylamine (II) may be carried out, as needed, to further purify fosaprepitant dicyclohexylamine (II).

Fosaprepitant dicyclohexylamine (II) prepared by the process of the present invention has a purity level greater than or equal to 99.0%, as measured by HPLC (hereinafter, "HPLC purity"). It may contain a low level of one or more impurities. Fosaprepitant dicyclohexylamine (II) has an HPLC purity of, preferably, greater than 99.5% (i.e., less than about 0.5% of impurities); more preferably, greater than 99.85% (i.e., less than about 0.15% of impurities); and even more preferably, greater than 99.9% (i.e., less than about 0.1% of impurities). The HPLC used herein refers to a reverse phase HPLC, using a Hypersil C8 250 mM column, and the eluant being a gradient of phosphate buffer (pH 3.5) and acetonitrile. The flow rate is 1 ml/min; and UV detector is set at a wavelength of 210 nM.

Figure 2:
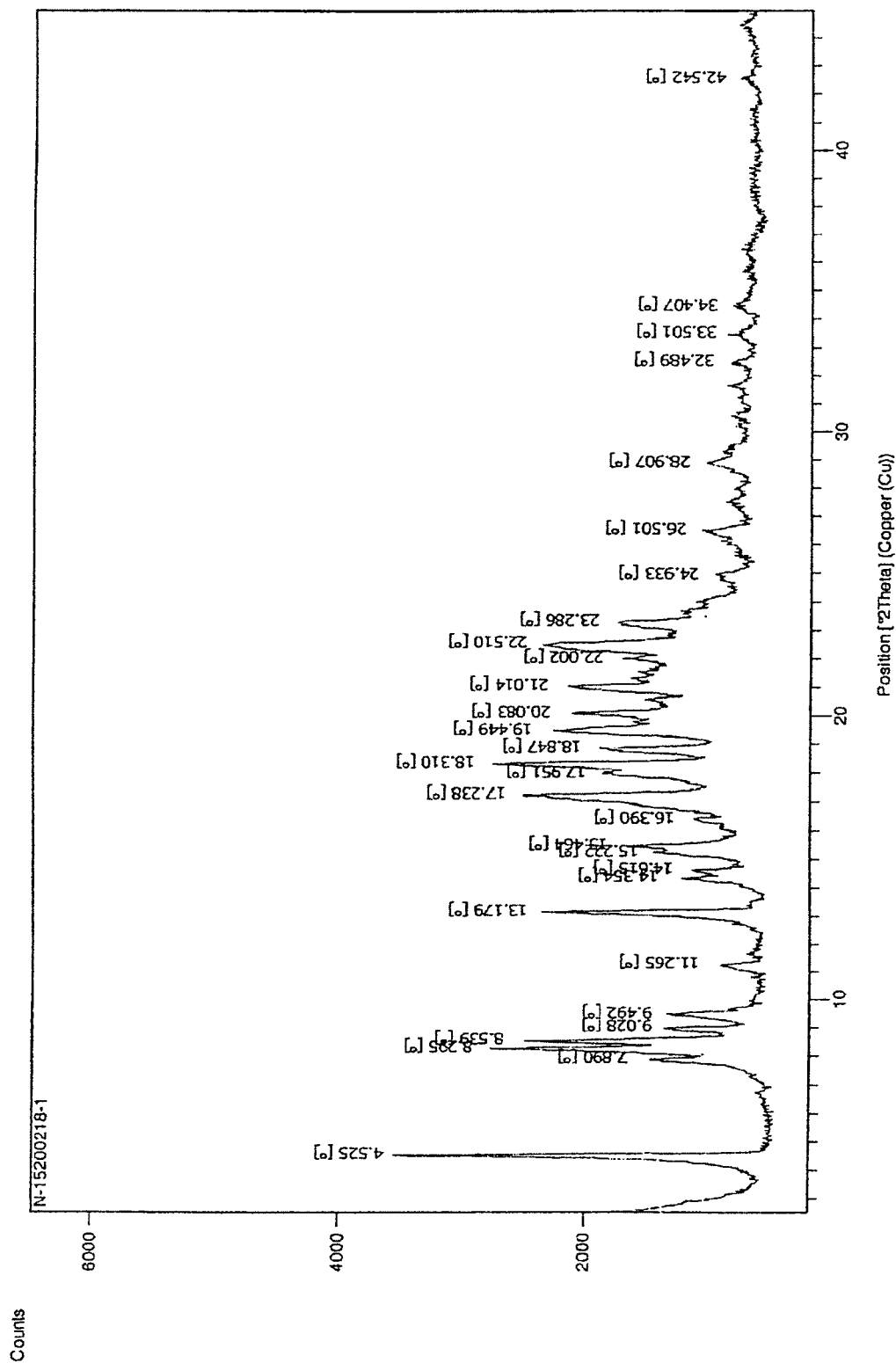
FIG. 2 shows an X-ray powder diffraction pattern of fosaprepitant DCHA salt (II) according to one embodiment of the invention.

Accordingly, the present invention provides a novel compound of fosaprepitant dicyclohexylamine (II) with high purity and a preparation method thereof, from aprepitant (III) to fosaprepitant dicyclohexylamine (II), as depicted in FIG. 1. According to some embodiments, an X-ray powder diffraction pattern of fosaprepitant DCHA salt is shown in FIG. 2. The X-ray powder diffraction pattern shows peaks at about 4.52, 8.29, 13.17, 17.23, 18.31, and 22.51±0.2° 2θ. The X-ray scans 2Theta range from 5 to 50, at an increment of 0.05.

Figure 3:
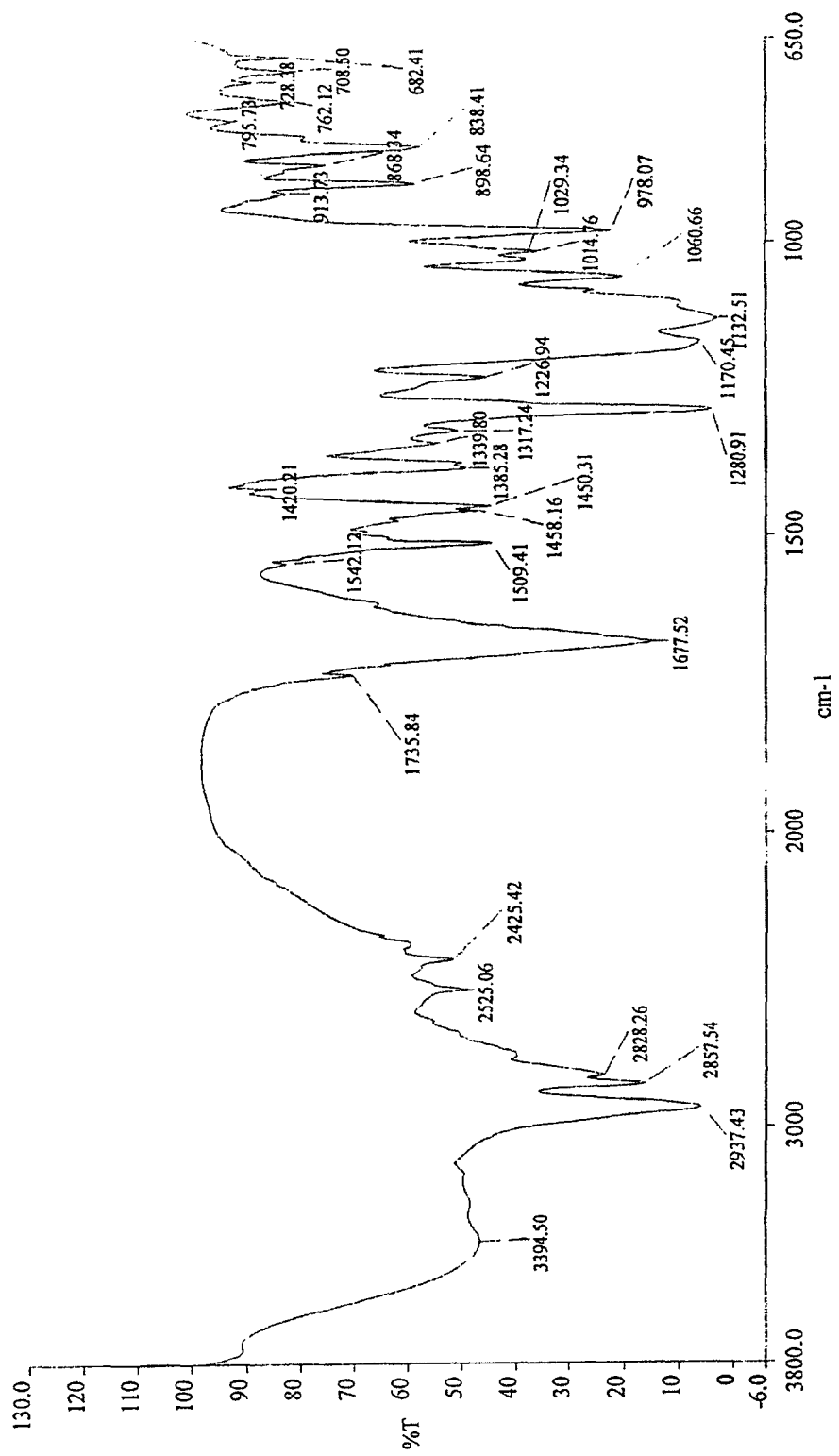
FIG. 3 shows Fourier transform IR spectra of fosaprepitant DCHA salt (II) according to one embodiment of the invention.

According to other embodiments, Fourier transform IR spectra of fosaprepitant DCHA salt is shown in FIG. 3, which show absorptions at about 1061, 1133, 1170, 1281, 1450, 1509, 1678, 2525, 2858, 2937, and 3395 cm$^{-1}$. The IR spectra is measured at using KBr pallet and scanning a range of 650-3800 cm$^{-1}$.

Referring back to FIG. 1, fosaprepitant dicyclohexylamine salt (II) may be treated with an aqueous or alcoholic hydrochloric acid in the presence of a protic or aprotic organic solvent to give fosaprepitant (I), which is then reacted with N-methyl-D-glucamine in the presence of an organic solvent to give fosaprepitant dimeglumine salt (Ia).

In accordance with some embodiments, the conversion from fosaprepitant dicyclohexylamine salt (II) to fosaprepitant dimeglumine salt (Ia) comprises the steps of:

1. adding fosaprepitant dicyclohexylamine salt (II) in an alcoholic solvent, preferably methanol, ethanol or isopropyl alcohol, or mixture of two or more of the solvents, to form a solution;

2. adding aqueous HCl or methanolic HCl or ethanolic HCl or isopropyl alcohol ("IPA") HCl to the solution of step 1 at a temperature in the range from about 0° C. to about 25° C., preferably about 5° C. to about 15° C.;

3. adjusting the pH of the reaction mixture of step 2 until the pH value is from about 1.0 to about 3.0, preferably from about 1.5 to about 2.5 at a temperature in the range from about 0° C. to about 25° C., preferably from about 5° C. to about 15° C.;

4. filtering the solid fosaprepitant (I) obtained step 3;

5. adding the solid of step 4 in an alcoholic solvent, preferably methanol, ethanol, isopropyl alcohol, n-butanol, or a mixture of two or more of the solvents to form a solution;

6. adding N-methyl-D-glucamine to the solution of step 5 at a temperature in the range from about 10° C. to about 50° C., preferably from about 20° C. to about 35° C., followed by maintaining the reaction mass at the same temperature for about 20 to about 80 minutes, preferably about 30 to about 45 minutes;

7. Optionally, filtering the mixture of step 6 to obtain a solution of fosaprepitant dimeglumine salt (Ia); and 8. adding the solution of fosaprepitant dimeglumine salt (Ia) of step 7 into a second solvent, preferably isopropyl alcohol, acetonitrile, acetone, ethyl acetate, isopropyl acetate, methyl ethyl ketone, or a mixture of two or more of the solvents, at a temperature in the range from about 10° C. to about 40° C., preferably from about 20° C. to about 30° C., to form fosaprepitant dimeglumine (Ia) followed by isolating fosaprepitant dimeglumine (Ia).

Fosaprepitant dimeglumine (Ia) prepared by the process of the present invention has a purity level greater than or equal to 99.0% by HPLC. It has very low level of one or more impurities. Fosaprepitant dimeglumine (Ia) contains, preferably, less than about 0.5% of impurities; more preferably, less than about 0.15% of impurities; and even more preferably, less than about 0.10% impurities, as measured by HPLC. In other words, fosaprepitant dimeglumine (Ia) has an HPLC purity of, preferably, greater than 99.5%, more preferably 99.85%; and even more preferably, greater than 99.9%.

As disclosed before, fosaprepitant DCHA (II) is a stable, easy to purify solid. Fosaprepitant DCHA (II) can be purified by crystallization. A person skilled in the art would understand that crystallization is an effective and efficient method to obtain a pure solid. A crystalline form solid generally has a higher melting point and high purity and is much more stable than an amorphous solid of the same kind. Compared to other common purification methods, such as flash column chromatography method, crystallization method greatly saves the consumption of solvents and silica gel. Crystallization method is also less time consuming and not labor intensive compared to flash column chromatography purification method. Crystallization purification is compatible to an industrial scale synthesis. It is noticed that crystallization of fosaprepitant DCHA (II) effectively leads to a solid free or substantially free from impurities.

In some embodiments, the fosaprepitant DCHA (II) made by the present invention has less than 10 ppm palladium level with even one crystallization, as measured by an atomic absorption spectroscopy or inductively coupled plasma atomic emission spectroscopy. Multiple crystallization processes may further reduce the palladium level in the fosaprepitant DCHA (II).

The conversion from fosaprepitant di(dicyclohexylamine) salt (II) to fosaprepitant dimeglumine (Ia) involves the addition of solvents, acids, and bases, and the production of a base (i.e. dicyclohexylamine) and water as byproducts. Because the excess solvents and reagents and byproducts are all water soluble, they may be easily and completely filtered, extracted, and washed away from fosaprepitant dimeglumine (Ia). As such, the high purity level of fosaprepitant di(dicyclohexylamine) salt (II) can be maintained and passed to fosaprepitant dimeglumine (Ia), with no new impurity introduced. By the term "impurity" or "impurities", it refers to excess reagents, byproducts, solvents, etc.

In comparison, there lacks an efficient method to purify the intermediates of dibenzyl ester and monobenzyl ester in the prior art processes. The impurities in the intermediates are passed, through debenzylation, to the product, fosaprepitant dimeglumine. Moreover, during the debenzylation, a catalyst, such as Pd on carbon, is introduced into the reaction mixture. The catalyst becomes an impurity when it is not completely removed. Because it is not easy to purify fosaprepitant or fosaprepitant dimeglumine, Pd on carbon may remain in fosaprepitant and its dimeglumine salt.

The material needed for preparing the di(dicyclohexylamine) salt (namely, dicyclohexylamine) is cheap and readily available. The conversation from the di(dicyclohexylamine) salt (II) to the dimeglumine salt (Ia) may be easily formed in one pot. As shown in FIG. 1, the di(dicyclohexylamine) salt (II) is converted to the free acid (I); and without isolating the free acid (I), the free acid (I) is transformed to the dimeglumine salt (Ia). The square bracket in FIG. 1 indicates that it is optional to isolate and purify the free acid (I) before using it in the next reaction step. One skilled in the art would appreciate that one pot reaction greatly avoids loss of yield during purification and isolation, and that one pot reaction is particularly amenable to a large, industrial scale synthesis. In some embodiments, the scale is greater than 10 Kg; in other embodiments, the scale is 20-30 Kg. But suitable reaction scales are not limited to such scales. One skilled in the art would appreciate that the present invention is suitable for any scale synthesis, from a small lab scale to a large industrial scale.

Therefore, the process for preparing fosaprepitant dimeglumine (Ia) in accordance with the present invention is simple, cost effective, and well suited for use on an industrial scale.

The present application is further illustrated in detail by the below examples, which, however, should not be construed to limit the scope of the invention in any manner.

EXAMPLES

Example 1. Synthesis of Fosaprepitant DCHA Salt (II)

To a solution of dibenzyl fosaprepitant (prepared from aprepitant as per prior art processes) in ethyl acetate (1000 mL), dicyclohexylamine (74.64 g, 0.41 mol), 10% Pd/C (50% wet) (25 g), basic alumina (20 g) and 20 mL of water were added and were stirred under a hydrogen pressure at a temperature of about 25° C. to about 30° C. till reaction completion. The reaction mass was filtered through hyflow and the solvent was from the filtrate by distillation. Acetone (1000 mL) was added to precipitate the solid fosaprepitant DCHA salt (II). The solid was filtered and dried (140 g, 75.6% yield), having a HPLC purity of 99.0%.

Example 2. Synthesis of Fosaprepitant Dimeglumine (Ia)

Fosaprepitant DCHA (II) (140 g) was dissolved in 1000 mL of Methanol. Aqueous HCl was added to adjust pH to about 2.0 and stirred to precipitate the solid fosaprepitant (I). The solid was filtered and added to in 400 mL of Methanol, and N-Methyl-D-glucamine (70 g, 0.358 mol) was added. The reaction mixture was stirred for about 20 to 30 minutes and the mixture was filtered. The filtrate was added into a mixture of acetonitrile (3500 mL) and isopropyl alcohol (1700 mL) to crystallize fosaprepitant dimeglumine (Ia). The fosaprepitant dimeglumine was filtered and dried under vacuum at 25° C. to 35° C. to offer fosaprepitant dimeglumine (Ia) (110 g, 58.5% yield), having a HPLC purity of 99.9%.

Example 3. Synthesis of Fosaprepitant Dimeglumine (Ia)

To a solution of dibenzyl fosaprepitant (prepared as per prior art processes) in ethyl acetate (1000 mL), dicyclohexyl amine (74.64 g, 0.41 mol), 10% Pd/C (50% wet) (25 g), basic alumina (20 g), and 20 mL of water were added and were stirred under a hydrogen pressure at a temperature of about 25° C. to 30° C. until reaction completion. The reaction mass was filtered through hyflow and removed the solvent from the filtrate by distillation to obtain residue of fosaprepitant DCHA (II). The residue was dissolved in 1000 mL of Methanol. Aqueous HCl was added to adjust pH about 2.0 and stirred to precipitate the solid fosaprepitant (I). The fosaprepitant solid was filtered and added in 400 mL of Methanol, N-Methyl-D-glucamine (70 g, 0.358 mol) was added. The resulting reaction mixture was stirred for about 20 to 30 minutes and filtered. The filtrate was added into a mixture of acetonitrile (3500 mL) and isopropyl alcohol (1700 mL) to crystallize fosaprepitant dimeglumine (Ia). The fosaprepitant dimeglumine solid was filtered, dried under vacuum at a temperature from about 25° C. to about 35° C. to obtain fosaprepitant dimeglumine (Ia) (125 g, 66.48% yield) having a HPLC purity of 99.5%.

Example 3 shows that fosaprepitant DCHA (II) formed during the process needs not to be isolated or crystallized as in Example 1. Example 3 represents an efficient in situ, one pot process for preparing fosaprepitant dimeglumine (Ia) via fosaprepitant DCHA (II).

It should be noted that the invention in its broader aspects is not limited to the specific details, representative compositions, methods, and processes, and illustrative examples described in connection with the preferred embodiments and preferred methods. Modifications and equivalents will be apparent to practitioners skilled in this art and are encompassed within the spirit and scope of the appended claims.

What is claimed is:

1. A process for the preparation of fosaprepitant di(N-methyl-D-glucamine) salt of formula Ia:

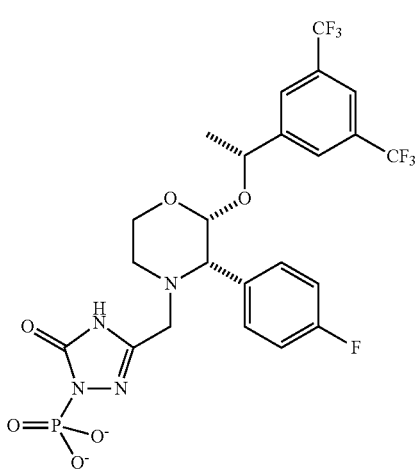

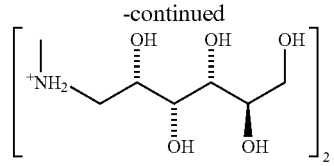

comprising:
(1) adding crystalline fosaprepitant di(dicyclohexylamine) salt of formula II in a solvent to form a solution and treating the solution with an acid to obtain fosaprepitant of formula I, wherein the crystalline fosaprepitant di(dicyclohexylamine) salt of formula (II) has a X-ray powder diffraction pattern with peaks at about 4.52, 8.29, 13.17, 13.23, 18.31, and 22.51±0.2°2θ

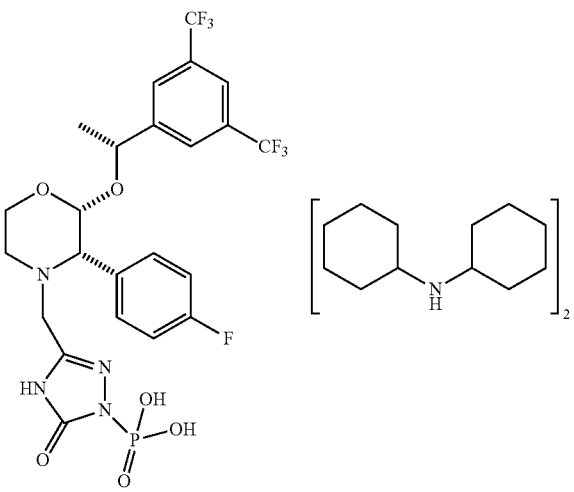

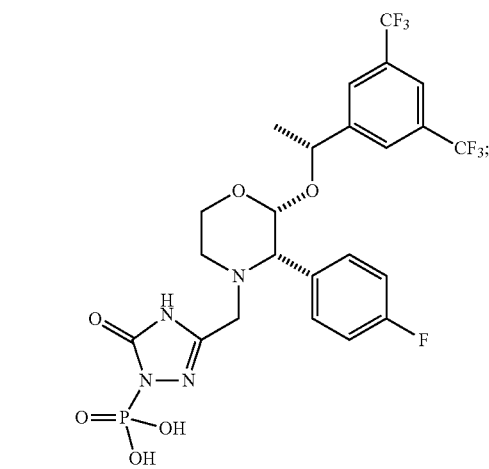

(2) dissolving fosaprepitant of formula I and N-methyl-D-glucamine in a first solvent to obtain a solution of fosaprepitant di(N-methyl-D-glucamine) salt of formula Ia; and
(3) isolating fosaprepitant di(N-methyl-D-glucamine) salt of formula Ia.

2. The process according to claim 1, wherein the first solvent in step (2) is selected from the group consisting of methanol, ethanol, isopropyl alcohol, and mixtures thereof.

3. The process according to claim 1, wherein the step of isolating fosaprepitant di(N-methyl-D-glucamine) salt of formula Ia is carried out by adding a second solvent.

4. The process according to claim 3, wherein the second solvent is selected from the group consisting of ethanol, isopropyl alcohol, acetonitrile, acetone, ethyl acetate, isopropyl acetate, methyl ethyl ketone, and mixtures thereof.

5. The process according to claim 1, wherein step (1) further comprises adjusting the pH of the reaction mixture until the pH value is from about 1.0 to about 3.0 after treating with the acid.

6. The process according to claim 1, wherein step (1) occurs at a temperature in a range from about 0° C. to about 25° C.

7. The process according to claim 6, wherein step (1) occurs at the temperature in the range from about 5° C. to about 15° C.

8. The process according to claim 1, wherein step (2) occurs at a temperature in a range from about 10° C. to about 50° C.

9. The process according to claim 8, wherein the solution of step (2) is maintained at about 10° C. to about 50° C. for about 20 to 80 minutes.

10. The process according to claim 8, wherein step (2) occurs at a temperature in a range from about 20° C. to about 35° C.

11. The process according to claim 8, wherein the solution of step (2) is maintained at about 10° C. to about 50° C. for about 30 to 45 minutes.

12. The process according to claim 3, wherein the second solvent is added at a temperature in a range from about 10° C. to about 40° C.

13. The process according to claim 12, wherein the second solvent is added at the temperature in the range from about 20° C. to about 30° C.

14. The process according to claim 1, wherein palladium in the crystalline fosaprepitant di(dicyclohexylamine) salt of formula II is less than 10 ppm.

15. The process according to claim 1, wherein the fosaprepitant di(N-methyl-D-glucamine) salt of formula Ia is substantially free of palladium.

16. The process according to claim 1, wherein the fosaprepitant di(N-methyl-D-glucamine) salt of formula Ia has a purity level of greater than 99.0% as measured by HPLC.

17. The process according to claim 1, wherein the crystalline fosaprepitant di(dicyclohexylamine) salt of formula II has Fourier transform IR spectra which shows absorptions at about 1061, 1133, 1170, 1281, 1450, 1509, 1678, 2525, 2858, 2937, and 3395 $cm^{-1}$.

18. The process according to claim 1, wherein the crystalline fosaprepitant di(dicyclohexylamine) salt of formula II has less than about 0.5% of impurities.

* * * * *